United States Patent
Lee et al.

(10) Patent No.: US 10,196,661 B2
(45) Date of Patent: Feb. 5, 2019

(54) CELLULASE-PRODUCING NOVEL STRAIN AND SACCHARIFICATION METHOD USING THE SAME

(71) Applicant: SK CHEMICALS CO., LTD., Seongnam-si, Gyeonggi-do (KR)

(72) Inventors: Jung Kul Lee, Seoul (KR); Tae Su Kim, Seoul (KR); Sujit Sadashiv Jagtap, Seoul (KR); Min Ho Cha, Seoul (KR); Jong In Lee, Seoul (KR); Hang Duk Roh, Hwaseong-si (KR)

(73) Assignee: SK CHEMICALS CO., LTD., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/483,337

(22) Filed: Apr. 10, 2017

(65) Prior Publication Data

US 2017/0226548 A1    Aug. 10, 2017

Related U.S. Application Data

(63) Continuation of application No. 14/380,818, filed as application No. PCT/KR2013/001406 on Feb. 21, 2013.

(30) Foreign Application Priority Data

Feb. 24, 2012    (KR) .................. 10-2012-0019335

(51) Int. Cl.
| | |
|---|---|
| C12P 19/02 | (2006.01) |
| C12N 9/42 | (2006.01) |
| C12P 19/14 | (2006.01) |
| C12R 1/645 | (2006.01) |
| C12N 1/14 | (2006.01) |

(52) U.S. Cl.
CPC .............. *C12P 19/02* (2013.01); *C12N 1/14* (2013.01); *C12N 9/2437* (2013.01); *C12P 19/14* (2013.01); *C12R 1/645* (2013.01); *C12Y 302/01004* (2013.01)

(58) Field of Classification Search
CPC .................................................... C12P 19/02
See application file for complete search history.

(56) References Cited

FOREIGN PATENT DOCUMENTS

| | | |
|---|---|---|
| CN | 101735952 A | 6/2010 |
| EP | 2286664 A1 | 2/2011 |
| KR | 1020100100201 A | 9/2010 |

OTHER PUBLICATIONS

Helal G. A. Mycobiology, 2005, 33(2):90-96.*
G.Q. Zhang et al., "A novel lectin with antiproliferative activity from the medicinal mushroom *Pholiota adiposa*", Acta Biochimica Polonica, Jul. 27, 2009, pp. 415-421, vol. 56, No. 3.
Yun-Xiang Wang et al., "Statistical optimization of media for extracellular polysaccharide by Pholiota squarrosa (Pers. ex Fr.) Quel. AS 5.245 under submerged cultivation", Biochemical Engineering Journal, Apr. 16, 2004, pp. 39-47.
Peng Deng et al., "Extraction and in vitro antioxidant activity of intracellular polysaccharide by Pholiota adiposa SX-02", Journal of Bioscience and Bioengineering, Aug. 6, 2010, pp. 50-54, vol. 111, No. 1.
International Search Report for PCT/KR2013/001406 dated Jun. 21, 2013.
Jing-Yu Lui et al, "Effect of Different Cultivation Substrates on Extracellular Enzyme Activities of Pholiota adiposa", Acta Edulis Fungi, 2006, pp. 44-47.
Ian D. Reid, "Solid-state fermentations for biological delignification", Enzyme Microb. Technol., Dec. 1989, pp. 786-803, vol. 11.
Saurabh Sudha Dhiman et al., "Immobilization of Pholiota adiposa xylanase onto SiO2 nanoparticles and its application for production of xylooligosaccharides", Springer Science+Business Media B.V., Published on-line on Mar. 16, 2012, pp. 1307-1313.
Sujit Sadashiv Jagtap et al., "Saccharification of poplar biomass by using lignocelluases from Pholiota adiposa", Bioresource Technology 2012, pp. 264-272.
S. Jagtap et al., "Pholiota adiposa strain KJS714 18S ribosomal RNA gene, partial sequence; internal transcribed spacer 1, 5.8S ribosomal RNA gene, and internal transcribed spacer 2, complete sequence; and 28S ribosomal RNA gene, partial sequence," https://www.ncbi.nlm.nih.gov/nuccore/340748004?sat=17&satkey=17029722, Jul. 26, 2011, 1 page.
Korea Office Action dated Sep. 28, 2018, issued in corresponding Korean Patent Application No. 10-2012-0019335.

* cited by examiner

*Primary Examiner* — Bin Shen
(74) *Attorney, Agent, or Firm* — Hauptman Ham, LLP

(57) ABSTRACT

The present invention relates to the novel strain *Pholiota adiposa* SKU714, a method for producing cellulase from the strain and a method for saccharifying cellulose using the produced cellulase. Since the cellulase produced by the novel strain according to the present invention exhibits better saccharification yield than the existing saccharification enzymes, it can be used in various applications, including bioenergy production, textile industry, papermaking industry, detergent industry, feed industry, food industry, production of low-calorie foods, fermentation of food wastes, or the like.

5 Claims, 3 Drawing Sheets

Specification includes a Sequence Listing.

[Fig. 1]
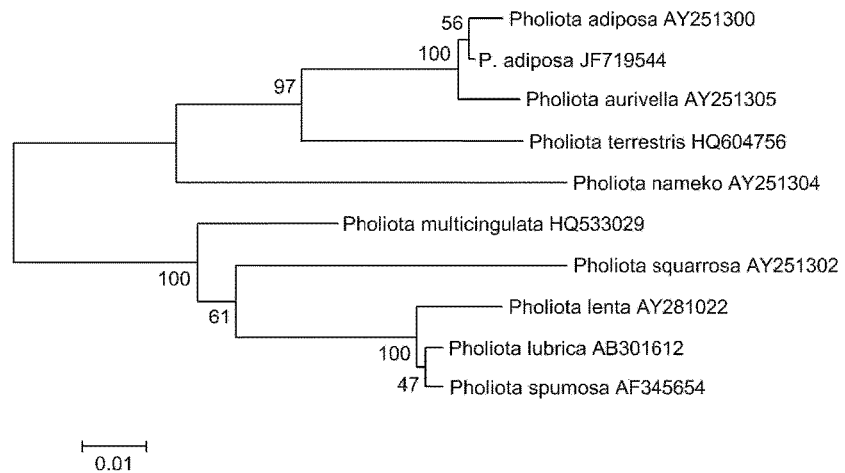
[Fig. 2a]
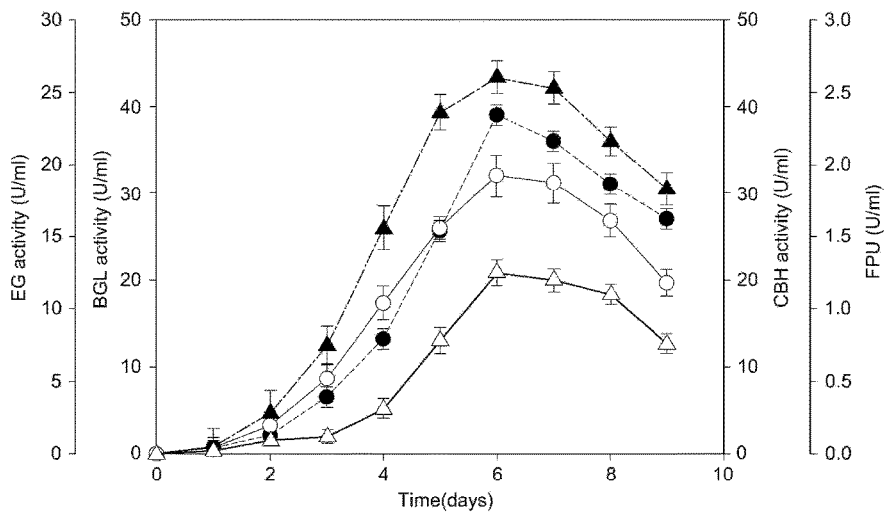

[Fig. 2b]
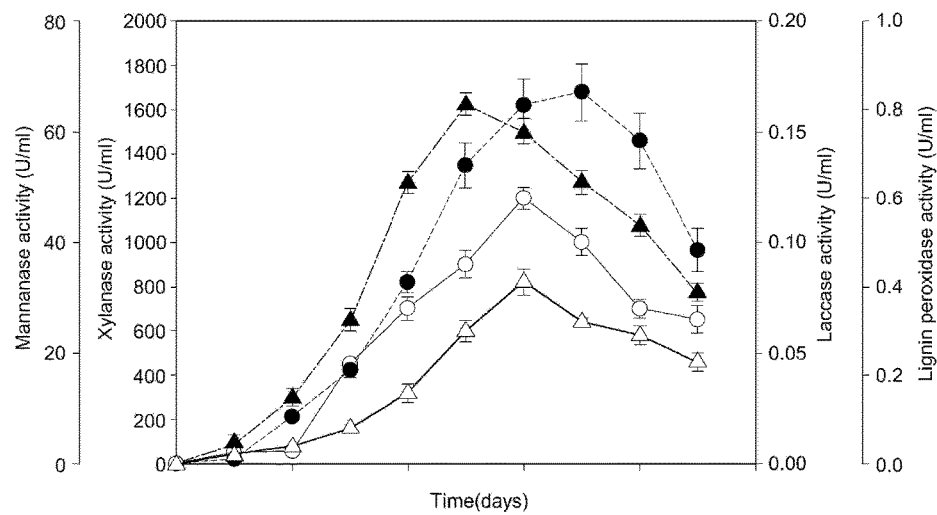
[Fig. 3a]
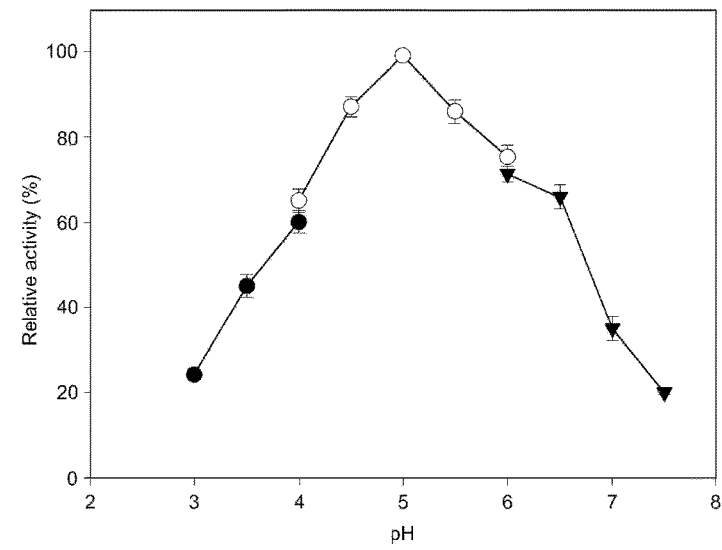

【Fig. 3b】
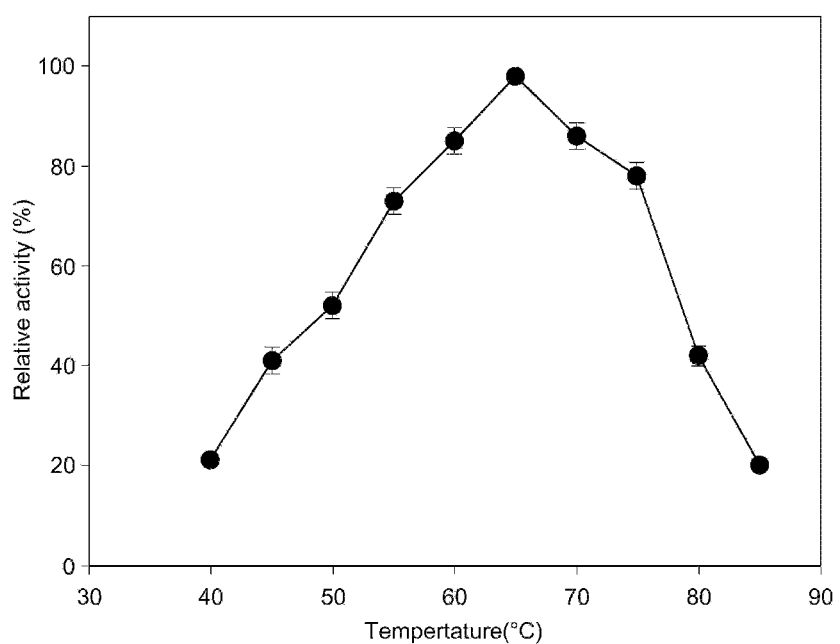

SEQUENCE LISTING

<160> NUMBER OF SEQ ID NOS: 1

<210> SEQ ID NO 1
<211> LENGTH: 592
<212> TYPE: DNA
<213> ORGANISM: Pholiota adiposa

<400> SEQUENCE: 1

```
aaggatcatt attgaatgaa cttggtatga ttgttgctgg cccatctggg catgtgcacg      60
tctgccatct ttatctctcc acctgtgcac atattgtagg tctggaataa atttctgagg     120
caactcagta gtggggaatg ctgctgcaaa gcggctttgc ctgtaatttc agatctatgt     180
```

-continued

```
tttcatatac accataaaaa tgtaacagaa tgtaataatg ggtcttgtac ctataaacta    240
tatacaactt tcagcaacgg atctcttggc tctcgcatcg atgaagaacg cagcgaaatg    300
cgataagtaa tgtgaattgc agaattcagt gaatcatcga atctttgaac gcaccttgcg    360
ctccttggta ttccgaggag catgcctgtt tgagtgtcat taaattctca atcttattag    420
cttttgttaa taaagacttg gatgtggggg ggaaattttt ttgaaggttt ctcgcgagcc    480 ttctcccta aaatgcatta gctggtcgct cgcgcgaact gtctattggt gtgataatta    540
tctacgccat tgactaactg ccatagtagc accgcttcta atcgtcttcg ga           592
```

CELLULASE-PRODUCING NOVEL STRAIN AND SACCHARIFICATION METHOD USING THE SAME

CROSS-REFERENCE TO RELATED APPLICATION

This present application is a continuation of U.S. patent application Ser. No. 14/380,818 filed on Jan. 21, 2015, which is a National Phase of International Patent Application No. PCT/KR2013/001406, filed Feb. 21, 2013, which claims priority to Korean Patent Application No. 10-2012-0019335, filed on Feb. 24, 2012. The disclosures of the above-listed application are hereby incorporated by reference herein in their entirety.

TECHNICAL FIELD

The present invention relates to the novel strain *Pholiota adiposa* SKU714, a method for producing cellulase from the strain and a method for saccharifying cellulose using the produced cellulase.

BACKGROUND ART

Cellulose is the most abundant organic matter on Earth. It is a renewable resource with no concern of depletion unlike petroleum or coal. However, cellulose is mostly discarded as agricultural and forestry wastes, which are regarded as the major causes of environmental pollution. Each year, more than 3 billion tons of agricultural and forestry wastes are produced worldwide, and more than 800 million tons in Asia only.

Since the agricultural and forestry wastes are mostly composed of cellulose and hemicellulose, if they can be converted to monosaccharides including glucose through saccharification, it may be greatly helpful for solving food, fuel and environmental problems.

As a general method of recovering monosaccharides from agricultural and forestry wastes, a method of adding sulfuric acid and conducting saccharification at high temperature and pressure is known. However, this method is problematic in that expensive equipment that can endure the strong acid and high pressure is necessary, separation and recovery of monosaccharides are difficult because of production of various byproducts, production cost is high because of the need to dispose of the byproducts and the associated processes are environment-unfriendly. Because the general saccharification method is limited for commercial application, researches have been made on a more environment-friendly cellulose saccharification method that can replace it. In this regard, various saccharification enzymes have been developed and commercialized for various industrial fields. Also, their applications are actively being studied. As the saccharification enzyme, cellulase is widely used in textile, papermaking, detergent and feed industries. In addition, it is used to produce low-calorie foods, ferment food wastes, or the like.

The cell wall of a plant consists of polymers such as cellulose (insoluble β-1,4-glucan fiber), hemicellulose (non-cellulose-based polysaccharide) and lignin (complex polyphenol polysaccharide). Among the components, cellulose is present in highest quantity, followed by hemicellulose with xylan as a main constituent. The two components account for more than 50% of the total plant biomass. Cellulose is a homopolymer of glucose units linked by β-1,4 linkage. To break it down into monosaccharides, three types of enzymes, i.e., endo-β-1,4-glucanase (endo-β-1,4-) [EC 3.2.1.4], exo-β-1,4-glucanase [EC 3.2.1.91] and β-glucosidase, are necessary. Endo-glucanase cleaves β-1,4 glucose linkages randomly from inside and exo-glucanase cleaves breaks down a glucan into the disaccharide cellobiose at a non-reducing end. Cellobiose is finally broken down to glucose by β-glucosidase.

Cellulase is mostly produced using molds (fungi). In particular, it is produced industrially using *Aspergillus* and *Trichoderma*. Although *Trichoderma reesei* ZU-02 (*Trichoderma reesei* ATCC 56764) has been intensively studied as a representative cellulase-producing strain, enzyme concentration and activity are not sufficient enough to satisfy the industrial needs. For example, although the process of producing ethanol from biomass has many advantages in terms of recycling of resources, environment-friendliness of the produced fuel, etc., the ethanol production from the lignocellulosic substance is highly costly as compared to gasoline production. In the ethanol production process, the cost of producing saccharification enzyme accounts for about 60% of the total production cost.

Accordingly, there is a strong need for an effective saccharification process of cellulose, particularly on environment-friendly one using a new strain.

DISCLOSURE

Technical Problem

The present invention has been made to solve the above-described problems of the prior art.

The present invention is directed to providing a cellulase-producing novel strain exhibiting high activity.

The present invention is also directed to providing a method for producing cellulase using the strain.

The present invention is also directed to providing a method for saccharifying cellulose using the cellulase.

Technical Solution

In an aspect, the present invention provides a cellulase-producing *Pholiota adiposa* SKU714 (Accession No. KCCM 11187P) strain.

In another aspect, the present invention provides a method for producing cellulase, including culturing the *Pholiota adiposa* SKU714 (Accession No. KCCM 11187P).

In the method for producing cellulase according to the present invention, the culturing may be performed using a medium of pH 4.5-5.5 containing corn steep powder (5-10 g/L), yeast extract (1-5 g/L), potassium dihydrogen phosphate (3-7 g/L), potassium hydrogen phosphate (3-7 g/L), magnesium sulfate heptahydrate (1-5 g/L), thiamine hydrochloride (0.01-0.03 g/L) and a carbon source (10-30 g/L).

In the method for producing cellulase according to the present invention, the carbon source may be selected from a group consisting of cellulose, cellobiose, rice straw and avicel.

In the method for producing cellulase according to the present invention, the culturing may be performed under the condition of a stirring rate of 100-200 rpm, an aeration rate of 0.8-1.2 vvm and a culturing temperature of 25-30° C.

In another aspect, the present invention provides a method for saccharifying cellulose using the cellulase produced by the *Pholiota adiposa* SKU714 strain.

In the method for saccharifying cellulose according to the present invention, the saccharification may be performed under the condition of a substrate concentration of 5-25 wt %, a cellulase concentration of 1-45 FPU/g substrate, pH 4-7 and a temperature of 50-80° C.

In the method for saccharifying cellulose according to the present invention, poplar, rice straw or a mixture thereof may be used as a cellulose source or substrate.

Advantageous Effects

The novel strain *Pholiota adiposa* SKU714 according to the present invention, which is isolated from mushroom, produces high-activity cellulase.

Since the cellulase produced by the novel strain according to the present invention exhibits better saccharification yield than the existing saccharification enzymes, it can be used in various applications, including bioenergy production, textile industry, papermaking industry, detergent industry, feed industry, food industry, production of low-calorie foods, fermentation of food wastes, or the like.

BRIEF DESCRIPTION OF DRAWINGS

FIG. 1 shows a result of analyzing the genetic relationship between the ITS-5.8S rDNA sequence of the strain of the present invention and similar species.

FIG. 2a shows a result of measuring the β-glucosidase activity (-●-), cellobiohydrolase activity (-○-), endoglucanase activity (-▲-) and glucose production (-Δ-) through breakdown of filter paper per unit enzyme amount of the *Pholiota adiposa* SKU714 strain with culturing time.

FIG. 2b shows a result of measuring the xylanase activity (-●-), laccase activity (-○-), mannanase activity (-▲-), and lignin peroxidase activity (-Δ-) of the *Pholiota adiposa* SKU714 strain with culturing time.

FIG. 3a shows the activity of β-glucosidase produced by the *Pholiota adiposa* SKU714 strain depending on pH.

FIG. 3b shows the activity of β-glucosidase produced by the *Pholiota adiposa* SKU714 strain depending on temperature.

BEST MODE FOR CARRYING OUT INVENTION

The present invention will be described in more detail through examples. However, the scope of this invention is not limited by the examples.

Example 1. Screening of Cellulase-Producing Strain

For screening of cellulase-producing strains, 10 μL of a mushroom culture was suspended in 10 mL of physiological saline. 10 μL of the resulting suspension ($1\times10^4$ cfu mL$^{-1}$) was plated onto potato dextrose agar containing 2% carboxymethyl cellulose and incubated at 27° C. for 3 days. After colony was formed on the solid agar medium, the plate was stained with 0.1% Congo red and then destained with 1 M sodium chloride. Then, cellulase-producing mushroom strains were screened by selecting ones having halos produced by hydrolysis of cellulose around the colony.

Primary strains (S1-S6) were screened through this procedure. From the screened strains, the S4 strain exhibiting the best cellulose degrading ability was selected after testing on the solid agar medium containing carboxymethyl cellulose using the existing producing strain *Trichoderma reesei* ZU-02 as control (C).

Example 2. Identification of Strain

For identification of the S4 strain screened in Example 1, the ITS-5.8S rDNA sequence was analyzed by the Korean Culture Center of Microorganisms. The ITS-5.8S rDNA sequence of the S4 strain was named as SEQ ID NO 1.

As a result of analyzing the genetic relationship between the ITS-5.8S rDNA sequence of the S4 strain with similar species, the S4 strain was identified as *Pholiota adiposa* (FIG. 1).

The S4 strain was named as '*Pholiota adiposa* SKU714' and deposited at the Korean Culture Center of Microorganisms on Apr. 20, 2011 with Accession No. KCCM 11187P under the Budapest Treaty.

Example 3. Optimization of Medium for Producing Cellulase (1) Cellulase Activity Depending on Carbon Source Cellulase-producing activity of the *Pholiota adiposa* SKU714 strain depending on carbon source was tested in a 7-L fermentation tank. Cellulose, glucose, lactose, maltose, cellobiose, carboxymethyl cellulose, sucrose, xylan, rice straw and avicel were used as carbon source.

After inoculating the *Pholiota adiposa* SKU714 strain in a 50-mL flask containing 50 mL of a whole culture medium (potato starch 4 g/L, dextrose 20 g/L), the strain was cultured in a shaking incubator at 150 rpm and 25° C. for 5 days. 50 mL of the culture was inoculated a 50-mL flask containing a growth medium (corn steep powder 8 g/L, yeast extract 2 g/L, potassium dihydrogen phosphate 5 g/L, potassium hydrogen phosphate 5 g/L, magnesium sulfate heptahydrate 3 g/L, thiamine hydrochloride 0.02 g/L and carbon source 20 g/L, pH 5) and cultured at 150 rpm, 25° C. and pH 5 for 7 days.

The result of measuring the β-glucosidase activity and glucose production of the *Pholiota adiposa* SKU714 strain for each carbon source is shown in Table 1.

TABLE 1

| Carbon source (20 g/L) | β-Glucosidase activity (U/mL) | Glucose production through breakdown of filter paper per unit enzyme amount (U/mL) |
|---|---|---|
| Cellulose | 16.4 | 0.63 |
| Glucose | 3.45 | 0.15 |
| Lactose | 4.10 | 0.14 |
| Maltose | 8.60 | 0.31 |
| Cellobiose | 10.6 | 0.43 |
| Carboxymethyl cellulose | 3.52 | 0.13 |
| Sucrose | 3.42 | 0.12 |
| Xylan | 5.30 | 0.26 |
| Rice straw | 15.0 | 0.52 |
| Avicel | 14.9 | 0.61 |

As seen from Table 1, superior cellulase activity was achieved when cellulose, cellobiose, rice straw and avicel were used as carbon source. The maximum cellulase activity was achieved when cellulose was used as the carbon source.

(2) Cellulase Activity Depending on Nitrogen Source

Cellulase-producing activity of the *Pholiota adiposa* SKU714 strain depending on nitrogen source was tested in a 7-L fermentation tank. Yeast extract, peptone, corn steep powder, urea, ammonium sulfate, potassium nitrate, sodium nitrate and tryptone were used as nitrogen source.

A result of measuring the β-glucosidase activity and glucose production of the *Pholiota adiposa* SKU714 strain for each carbon source at a concentration of 5 g/L is shown in Table 2.

TABLE 2

| Nitrogen source (5 g/L) | β-Glucosidase activity (U/mL) | Glucose production through breakdown of filter paper per unit enzyme amount (U/mL) |
|---|---|---|
| Yeast extract | 18.6 | 0.72 |
| Peptone | 11.8 | 0.45 |
| Corn steep powder | 18.5 | 0.70 |
| Urea | 14.5 | 0.31 |
| Ammonium sulfate | 6.0 | 0.24 |
| Potassium nitrate | 11.1 | 0.36 |
| Sodium nitrate | 10.7 | 0.34 |
| Tryptone | 14.6 | 0.69 |

As seen from Table 2, superior cellulase activity was achieved when yeast extract, corn steep powder and tryptone were used as nitrogen source. The maximum cellulase activity was achieved when yeast extract was used as the nitrogen source.

Example 4. Optimization of Culturing Condition for Production of High-Activity Enzyme (1) Optimization of Culturing Condition when Poplar is Used as Substrate Culturing condition was optimized in a 7-L fermentation tank using a medium containing corn steep powder (8 g/L), yeast extract (2 g/L), potassium dihydrogen phosphate (5 g/L), potassium hydrogen phosphate (5 g/L), magnesium sulfate heptahydrate (3 g/L), thiamine hydrochloride (0.02 g/L) and poplar (20 g/L). Cellulase activity was compared while varying pH from 3 to 7 and changing culturing temperature from 20 to 35° C. The maximum cellulase activity was achieved at pH 5 and 25-30° C.

Also, the activity of each cellulase with culturing time was measured at the optimized culturing condition (pH 5, 25° C.) in the medium containing the poplar substrate (FIGS. 2a and 2b). FIG. 2a shows a result of measuring β-glucosidase, cellobiohydrolase and endoglucanase activities and glucose production through breakdown of filter paper per unit enzyme amount with culturing time. FIG. 2b shows a result of measuring the change in xylanase, laccase, mannanase and lignin peroxidase activities with culturing time.

(2) Optimization of Cellulase Production and Activity when Rice Straw is Used as Substrate Culturing condition was optimized in a 7-L fermentation tank using a medium containing corn steep powder (8 g/L), yeast extract (2 g/L), potassium dihydrogen phosphate (5 g/L), potassium hydrogen phosphate (5 g/L), magnesium sulfate heptahydrate (3 g/L), thiamine hydrochloride (0.02 g/L) and rice straw (20 g/L). Cellulase production was compared while varying pH from 3 to 7 and changing culturing temperature from 20 to 35° C. The maximum cellulase production was achieved at pH 5 and 25-30° C.

Also, β-1,4-glucosidase activity was compared while varying pH from 3 to 7.5 and changing temperature from 40 to 85° C. The result is shown in FIGS. 3a and 3b. As seen from FIGS. 3a and 3b, the maximum cellulase activity was achieved at pH 5 and 65° C.

Example 5. Analysis of Saccharification Yield

In general, lignocellulose contained in a plant cannot be saccharified at high yield only with enzymatic hydrolysis. For this reason, lignin and hemicellulose are fragmented prior to enzymatic hydrolysis through a pretreatment process in order to increase the cellulose hydrolysis efficiency by cellulase. In Example 5, for the pretreatment, 10 g of rice straw was added to a flask containing 40 mL of 2 wt % sodium hydroxide solution and reacted at 85° C. for 1 hour. Then, the rice straw was filtered through a 0.45-uM filter and dried at 65° C.

In order to find the optimized saccharification condition, experiment was conducted while varying enzyme concentration, substrate concentration, reaction temperature and reaction pH.

First, the pretreated rice straw at various concentrations was added to 20 mL of 0.1 M sodium acetate buffer (pH 5.0) together with cellulase at various concentrations. After reaction at 15-55° C. and 150 rpm for 72 hours, the reaction mixture was boiled at 100° C. for 3 minutes to remove denatured enzyme, which was then cooled to room temperature and centrifuged at 4000 rpm for 15 minutes. Enzyme activity was measured by the reducing sugar method from the supernatant.

Saccharification yield was determined according to Equation 1 by measuring the weight decrease of the rice straw after drying at 105° C. for 24 hours per gram of the rice straw.

Saccharification yield (%)=[(Weight of produced reducing sugar/g substrate)×0.9/Weight of carbohydrate in rice straw]×100   [Equation 1]

(1) Saccharification Yield Depending on Enzyme Concentration

Saccharification was performed using *Pholiota adiposa* SKU714 strain at 65° C. and pH 6 while varying enzyme concentration. The result is shown in Table 3.

TABLE 3

| Enzyme concentration (FPU/g substrate) | Saccharification yield (%) |
|---|---|
| 1 | 9.7 |
| 5 | 23.9 |
| 17.5 | 83.0 |
| 30 | 81.2 |
| 42.5 | 80.6 |

As seen from Table 3, the best saccharification yield was achieved when the enzyme concentration was 15-45 FPU/g substrate.

(2) Saccharification Yield Depending on Substrate Concentration

The effect of substrate concentration on the saccharification of poplar by the saccharification enzyme produced by the *Pholiota adiposa* SKU714 strain was investigated. Saccharification yield was measured while varying the initial concentration of the poplar substrate from 1 to 27 wt %. The result is shown in Table 4.

TABLE 4

| Substrate concentration (wt %) | Saccharification yield (%) |
|---|---|
| 1 | 43.0 |
| 2 | 63.5 |
| 11 | 81.2 |
| 20 | 83.1 |
| 27 | 51.0 |

As seen from Table 4, superior saccharification yield was achieved when the initial concentration of the poplar substrate was 10-25 wt %. The best saccharification yield was achieved when the poplar concentration was 20 wt %.

(3) Saccharification Yield Depending on Temperature

The effect of temperature on the saccharification of poplar by the saccharification enzyme produced by the *Pholiota adiposa* SKU714 strain was investigated. Saccharification yield was measured at different reaction temperatures of 20, 35, 50, 65 and 80° C. The result is shown in Table 5.

TABLE 5

| Reaction temperature (° C.) | Saccharification yield (%) |
| --- | --- |
| 20 | 33.2 |
| 35 | 45.0 |
| 50 | 75.8 |
| 65 | 82.1 |
| 80 | 71.2 |

As seen from Table 5, superior saccharification yield was achieved when the saccharification temperature was 50-80° C. The best saccharification yield was achieved at 65° C.

(4) Saccharification Yield Depending on pH

The effect of pH on the saccharification of poplar by the saccharification enzyme produced by the *Pholiota adiposa* SKU714 strain was investigated. Saccharification yield was measured at different reaction pH's of 1, 3, 5, 7 and 9. The result is shown in Table 6.

TABLE 6

| pH | Saccharification yield (%) |
| --- | --- |
| 1 | 20.0 |
| 3 | 62.6 |
| 5 | 81.4 |
| 7 | 84.0 |
| 9 | 39.4 |

As seen from Table 6, superior saccharification yield was achieved at pH 4-7. The best saccharification yield was achieved at pH 7.

Example 6. Saccharification Under Optimized Condition (1) Saccharification of Poplar Using *Pholiota adiposa* Cellulase Saccharification of poplar was conducted under the optimized condition using the cellulase produced by the *Pholiota adiposa* SKU714 strain. Saccharification was performed under the condition of a substrate concentration 10 wt %, an enzyme concentration 25 FPU/g substrate, pH 6 and a temperature 65° C. The saccharification yield of the cellulase produced by the *Pholiota adiposa* SKU714 strain is compared with that of Novozymes' cellulase derived from *Trichoderma reesei*(Celluclast 1.5L) in Table 7.

TABLE 7

| Cellulase | Sugar production (mg/g poplar) | Saccharification yield (%) |
| --- | --- | --- |
| *Pholiota adiposa* SKU714 | 672 | 84 |
| Celluclast 1.5 L | 242 | 35 |

(2) Saccharification of Rice Straw Using *Pholiota adiposa* Cellulase

Saccharification of rice straw was conducted under the optimized condition using the cellulase produced by the *Pholiota adiposa* SKU714 strain. Saccharification was performed for 24 hours under the condition of a substrate concentration 10 wt %, an enzyme concentration 16 FPU/g substrate, pH 6 and a temperature 65° C. The saccharification yield of the cellulase produced by the *Pholiota adiposa* SKU714 strain is compared with those of Novozymes' cellulase derived from *Trichoderma reesei* (Celluclast 1.5L) and cellulase derived from the *Pholiota nameko* KTCC26163 strain in Table 8.

TABLE 8

| Cellulase | Sugar production (mg/g rice straw) | Saccharification yield (%) |
| --- | --- | --- |
| *Pholiota adiposa* SKU714 | 690 | 88 |
| *Trichoderma reesei* | 582 | 76 |
| *Pholiota nameko* | 420 | 56 |

Although the *Pholiota nameko* and *Pholiota adiposa* strains belong to the same genus *Pholiota*, they exhibit quite different cellulose saccharification effects. Whereas the *Pholiota nameko* strain is limited for use as a saccharification enzyme due to low protein productivity and low enzyme activity, the *Pholiota adiposa* strain according to the present invention is suitable for commercial application owing to production of various biomass-degrading enzymes including cellulase, high protein productivity, high enzyme activity and good thermal stability.

[Accession No.]

Deposition agency: Korean Culture Center of Microorganisms

Accession No.: KCCM 11187P

Accession date: 20110420

The invention claimed is:

1. A method for saccharifying cellulose, comprising: a) culturing *Pholiota adiposa* SKU714 deposited under Accession No. KCCM 11187P to produce cellulase; and b) saccharifying a cellulose substrate using the produced cellulase, wherein the saccharification is performed under the condition of a substrate concentration of 5-25 wt %, the cellulase concentration of 15-45 filter paper unit per gram (FPU/g) substrate, pH 4-7 and a temperature of 50-80° C.

2. The method for saccharifying cellulose according to claim 1, wherein the cellulose substrate is poplar, rice straw or a mixture thereof.

3. The method for saccharifying cellulose according to claim 1, wherein
the cellulase is produced by culturing *Pholiota adiposa* SKU714 deposited under Accession No. KCCM 11187P, and
the culturing is performed in a medium of pH 4.5-5.5 containing corn steep powder (5-10 g/L), yeast extract (1-5 g/L), potassium dihydrogen phosphate (3-7 g/L), potassium hydrogen phosphate (3-7 g/L), magnesium sulfate heptahydrate (1-5 g/L), thiamine hydrochloride (0.01-0.03 g/L) and a carbon source (10-30 g/L).

4. The method for saccharifying cellulose according to claim 3, wherein the carbon source is at least one selected from the group consisting of cellulose, cellobiose, and rice straw.

5. The method for saccharifying cellulose according to claim 1, wherein the cellulase is produced by culturing *Pholiota adiposa* SKU714 deposited under Accession No. KCCM 11187P under the condition of a stirring rate of 100-200 rpm, an aeration rate of 0.8-1.2 vvm and a culturing temperature of 25-30° C.

* * * * *